(12) United States Patent
Scampoli et al.

(10) Patent No.: US 11,627,967 B2
(45) Date of Patent: Apr. 18, 2023

(54) TRANS-ANASTOMOTIC INSERTION DEVICE

(71) Applicant: Covidien LP, Mansfield, MA (US)

(72) Inventors: David Scampoli, South Glastonbury, CT (US); Thomas A. Zammataro, North Haven, CT (US); Patrick D. Mozdzierz, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/518,678

(22) Filed: Nov. 4, 2021

(65) Prior Publication Data

US 2022/0160362 A1     May 26, 2022

Related U.S. Application Data

(60) Provisional application No. 63/116,970, filed on Nov. 23, 2020.

(51) Int. Cl.
*A61B 17/064*     (2006.01)
*A61B 17/115*     (2006.01)
*A61B 17/00*     (2006.01)

(52) U.S. Cl.
CPC . *A61B 17/1155* (2013.01); *A61B 2017/00831* (2013.01)

(58) Field of Classification Search
CPC . A61B 17/068; A61B 17/115; A61B 17/1155; A61B 2017/00557; A61B 2017/07257; A61B 2217/007
See application file for complete search history.

(56) References Cited

U.S. PATENT DOCUMENTS

| | | | |
|---|---|---|---|
| 3,388,847 A | 6/1968 | Kasulin et al. | |
| 3,552,626 A | 1/1971 | Astafiev et al. | |
| 3,638,652 A | 2/1972 | Kelley | |
| 3,771,526 A | 11/1973 | Rudie | |
| 4,198,982 A | 4/1980 | Fortner et al. | |
| 4,207,898 A | 6/1980 | Becht | |

(Continued)

FOREIGN PATENT DOCUMENTS

| | | |
|---|---|---|
| CA | 908529 A | 8/1972 |
| CA | 2805365 A1 | 8/2013 |

(Continued)

*Primary Examiner* — Eyamindae C Jallow
(74) *Attorney, Agent, or Firm* — Carter, DeLuca & Farrell LLP (57) ABSTRACT

A trans-anastomotic insertion device includes a body having a distal portion, a proximal portion, and a central portion. The distal portion has a blunt distal end, a width that decreases from its distal end to its proximal end, and longitudinal ribs that provide rigidity to the distal portion. The central portion has a circular configuration and includes a proximally facing surface that includes protrusions that are positioned to be received within staple pockets of a reload assembly of a stapling device. The proximal portion includes a central post that includes splines that are received between splines on a shell housing of a stapling device. The configuration of the insertion device provides added strength to the insertion device to resist high torsional forces that may be applied to the insertion device during insertion of a surgical device through an incision into a body cavity.

20 Claims, 6 Drawing Sheets

(56) References Cited

U.S. PATENT DOCUMENTS

| | | |
|---|---|---|
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshln et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |

(56) References Cited

U.S. PATENT DOCUMENTS

| | | |
|---|---|---|
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,474 B2 * | 6/2005 | Borgesen ............ A61M 27/006 604/9 |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |

(56) References Cited

U.S. PATENT DOCUMENTS

| | | |
|---|---|---|
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |

(56) References Cited

U.S. PATENT DOCUMENTS

| | | |
|---|---|---|
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2001/0053933 A1* | 12/2001 | Phaneuf ............ C08G 18/10 |
| | | 623/1.48 |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0254002 A1* | 11/2007 | Wu ............ A61L 27/227 |
| | | 424/445 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |

(56) References Cited

U.S. PATENT DOCUMENTS

| | | |
|---|---|---|
| 2015/0083772 A1 | 3/2015 | Miller et al. |
| 2015/0173763 A1 | 6/2015 | Liu |
| 2015/0209045 A1 | 7/2015 | Hodgkinson et al. |
| 2017/0128068 A1 | 5/2017 | Zhang et al. |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3023077 A1 | 5/2016 |
| EP | 3412225 A1 | 12/2018 |
| EP | 3549545 A2 | 10/2019 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9835614 A1 | 8/1998 |
| WO | 0154594 A1 | 8/2001 |
| WO | 02080781 A2 | 10/2002 |
| WO | 2004047654 A2 | 6/2004 |
| WO | 2008107918 A1 | 9/2008 |
| WO | 2019130087 A1 | 7/2019 |

\* cited by examiner

TRANS-ANASTOMOTIC INSERTION DEVICE

CROSS-REFERENCE TO RELATED APPLICATION

This application claims the benefit of and priority to U.S. Provisional Patent Application No. 63/116,970, filed Nov. 23, 2020, the entire contents of which is incorporated by reference herein.

FIELD

The disclosure is directed to an insertion device for inserting a surgical instrument through a body incision and, more particularly, to a trans-anastomotic insertion device for inserting a circular stapling device through a body incision during a surgical procedure.

BACKGROUND

Circular stapling devices are commonly used to perform anastomoses during surgical procedures such as gastric bypass procedures. During a gastric bypass procedure, the circular stapling device is inserted through an incision in a patient into the patient's abdominal cavity to reroute the gastrointestinal tract. In order to minimize the size of the incision, a trans-anastomotic insertion device is attached to the circular stapling device to dilate the incision and facilitate passage of the circular stapling device into the abdominal cavity through the incision. During insertion of the trans-anastomotic insertion device and circular stapling device into the abdominal cavity, the trans-anastomotic insertion device is subjected to large insertion and torsion forces.

Trans-anastomotic insertion devices are available in reusable and disposable versions. Typically, the reusable version of a trans-anastomotic insertion device is formed from metal and the disposable version of a trans-anastomotic insertion device is formed from plastic. The disposable versions of the trans-anastomotic insertion devices are less expensive but are more prone to torsional breakage due the high forces that the trans-anastomotic insertion devices are subjected to during insertion into the abdominal cavity.

SUMMARY

This disclosure is directed to a trans-anastomotic insertion device that is releasably coupled to a surgical device to facilitate passage of the surgical device through an incision during minimally invasive surgical procedures. The insertion device is configured to resist high torsional forces that may be applied to the insertion device during the insertion of the surgical device into a body cavity through the incision.

One aspect of the disclosure is directed to a trans-anastomotic insertion device that includes a body that defines a longitudinal axis and has a distal portion, a proximal portion, and a central portion. The distal portion has a proximal end, a distal end, and a width that decreases from the proximal end towards the distal end. The distal end has a blunt distal surface. The distal portion includes longitudinal ribs that extend between the proximal and distal ends of the distal portion. The central portion has a circular configuration and includes a proximal surface and a distal surface. The proximal surface includes a plurality of protrusions that extend proximally from the proximal surface. The proximal portion has a central post that extends proximally from the central portion and includes a plurality of longitudinally extending splines positioned about the central post.

Other aspects of the disclosure are directed to a stapling device that includes a reload assembly and a trans-anastomotic insertion device. The reload assembly includes a shell housing and a staple cartridge. The shell housing has an annular inner body portion and an annular outer body portion. The annular inner body portion and the annular outer body portion define an annular cavity therebetween. The staple cartridge is supported on the shell housing within the annular cavity and includes a body having a distal face and defining a plurality of staple pockets. The annular inner body portion has an inner wall including a plurality of splines. The trans-anastomotic insertion device includes a body that defines a longitudinal axis and includes a distal portion, a proximal portion, and a central portion. The distal portion has a proximal end, a distal end, and a width that decreases from the proximal end towards the distal end. The distal end has a blunt distal surface. The distal portion includes longitudinal ribs that extend between the proximal and distal ends of the distal portion. The central portion has a circular configuration and includes a proximal surface and a distal surface. The proximal surface includes a plurality of protrusions that extend proximally from the proximal surface. The proximal portion has a central post that extends proximally from the central portion and includes a plurality of longitudinally extending splines positioned about the central post. The trans-anastomotic insertion device is releasably secured to the reload assembly such that the central post is received within the annular inner body portion of the shell housing and the protrusions extending from the proximal face of the central portion of the trans-anastomotic insertion device are received within the staple pockets of the body of the staple cartridge.

In aspects of the disclosure, the central portion includes an annular flange that is positioned on the distal surface about the distal portion.

In some aspects of the disclosure, the central post includes a proximal section that has resilient legs.

In certain aspects of the disclosure, each of the resilient legs includes a transverse extension that defines a stop surface.

In aspects of the disclosure, the proximal surface of the central portion supports a cylinder that is positioned about and is spaced from the central post.

In some aspects of the disclosure, the body is molded from a plastic material.

In certain aspects of the disclosure, the plurality of splines includes at least three splines.

In aspects of the disclosure, the distal portion of the trans-anastomotic insertion device includes planar side walls and the longitudinal ribs are positioned on the planar side walls.

In some aspects of the disclosure, each of the resilient legs includes a transverse extension that defines a stop surface and the annular inner body portion of the shell housing defines a shelf.

In certain aspects of the disclosure, the transverse extensions engage the shelf to retain the trans-anastomotic insertion device on the reload assembly.

In aspects of the disclosure, the cylinder is positioned about and engaged with the annular inner body portion of the shell housing when the trans-anastomotic insertion device is secured to the reload assembly.

In some aspects of the disclosure, the plurality of splines includes at least three splines.

In certain aspects of the disclosure, the stapling device includes an elongate body that has a proximal portion and a distal portion and the reload assembly is supported on the distal portion of the elongate body.

In aspects of the disclosure, the stapling device includes a handle assembly and the proximal portion of the elongate body is coupled to the handle assembly.

In some aspects of the disclosure, the handle assembly includes a stationary handle and actuation buttons.

In aspects of the disclosure, the distal portion of the trans-anastomotic insertion device includes planar side walls and the longitudinal ribs are positioned on the planar side walls.

Other features of the disclosure will be appreciated from the following description.

BRIEF DESCRIPTION OF THE DRAWINGS

Various aspects of the disclosed trans-anastomotic insertion device are described herein below with reference to the drawings, wherein.

DETAILED DESCRIPTION

The disclosed trans-anastomotic insertion device will now be described in detail with reference to the drawings in which like reference numerals designate identical or corresponding elements in each of the several views. However, it is to be understood that aspects of the trans-anastomotic insertion device disclosed are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Aspects of this disclosure are directed to a trans-anastomotic insertion device for inserting a surgical device through an incision into a patient for minimally invasive surgery. The trans-anastomotic insertion device includes a body that has a distal portion, a proximal portion, and a central portion. The distal portion supports longitudinal ribs and has a blunt distal end and a width that decreases from its distal end to its proximal end. The central portion has a circular configuration and includes a proximally facing surface that includes protrusions that are positioned to be received within staple pockets of a reload assembly of a stapling device. The proximal portion includes a central post that is received within a shell housing of the reload assembly and includes splines that are received between splines on the shell housing. The configuration of the insertion device provides added strength to the insertion device to resist the high torsional forces that may be applied to the insertion device during insertion of a surgical device into a body cavity through an incision.

Figure 1:
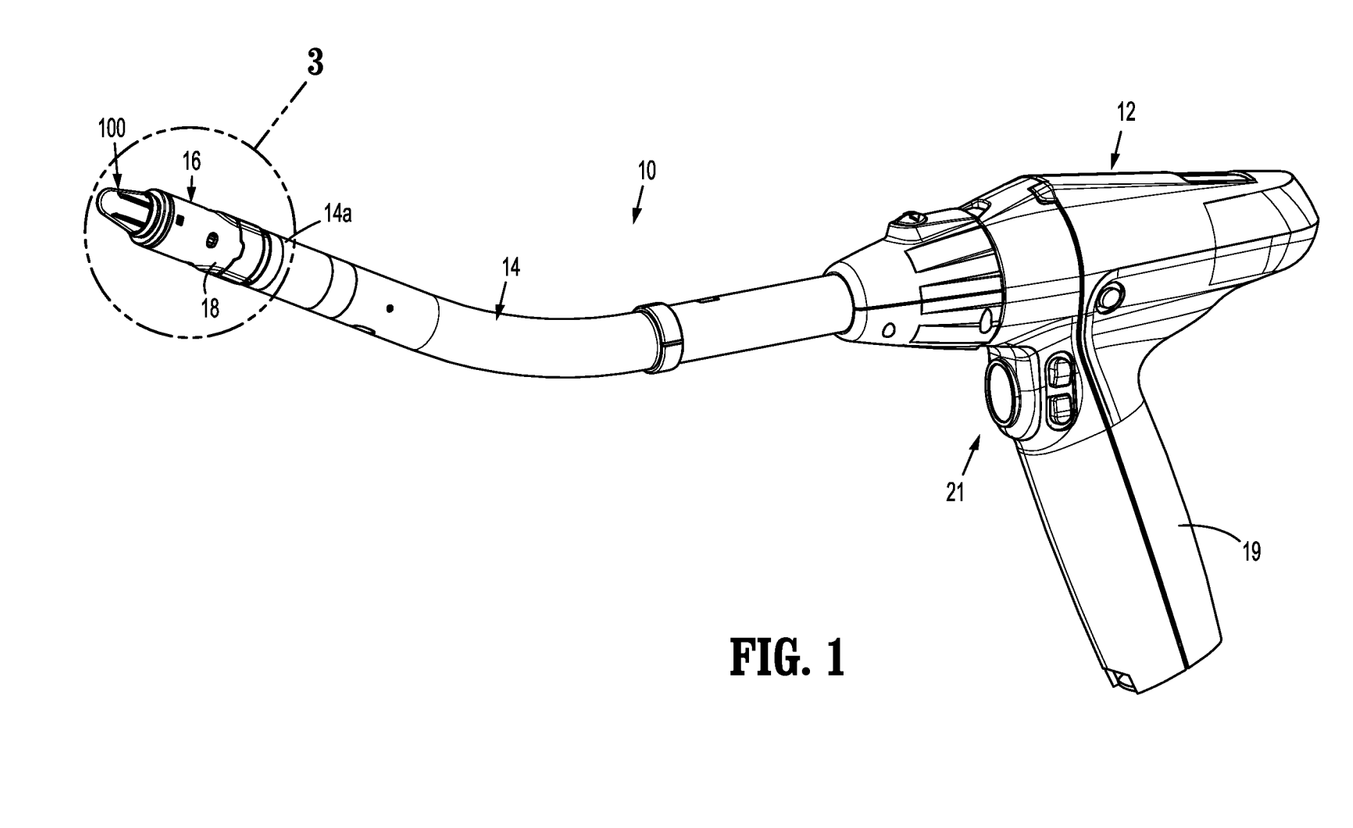
FIG. 1 is a side perspective view of a surgical stapling device with an anvil assembly removed and a trans-anastomotic insertion device according to aspects of the disclosure secured to a reload assembly of the surgical stapling device.
Figure 2:
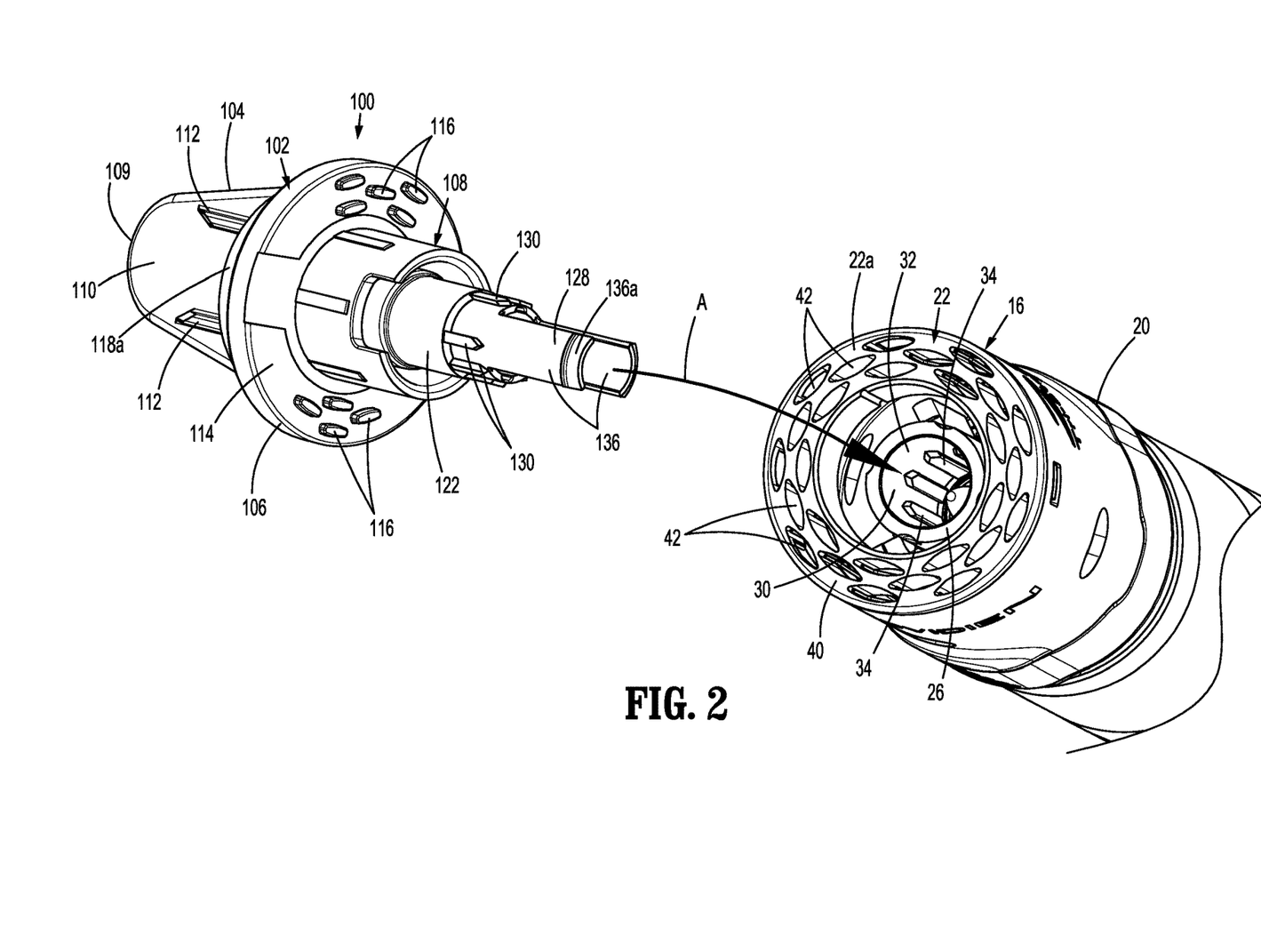
FIG. 2 is a side perspective view of the distal portion of the circular stapling device including the reload assembly and the trans-anastomotic insertion device shown in FIG. 1 with the trans-anastomotic insertion device separated from the circular stapling device.

FIGS. 1 and 2 illustrate a circular stapling device 10 with an anastomotic insertion device, shown generally as insertion device 100, according to aspects of the disclosure secured to a distal end of the circular stapling device 10. The stapling device 10 includes a handle assembly 12, an elongate body or adaptor assembly 14, and a reload assembly 16. An anvil assembly (not shown) is supported on a distal end of the adaptor assembly 14 and is movable in relation to the reload assembly 16 between spaced and clamped positions as is known in the art. In aspects of the disclosure, the reload assembly 16 includes a proximal portion 18 that is releasably coupled to a distal portion 14a of the elongate body 14. In certain aspects of the disclosure, the handle assembly 12 includes a stationary grip 19 that supports actuation buttons 21 for controlling operation of various functions of the stapling device 10 including approximation of the reload assembly 16 and the anvil assembly (not shown), firing of staples from the reload assembly 16, and cutting or coring of tissue.

The stapling device 10 is illustrated as an electrically powered stapling device including an electrically powered handle assembly 12 that may support one or more batteries (not shown). The elongate body 14 is in the form of an adaptor assembly that translates power from the handle assembly 12 to the reload assembly 16 and the anvil assembly (not shown). Examples of electrically powered stapling devices including an anvil assembly can be found in U.S. Pat. Nos. 9,055,943, 9,023,014, and U.S. Publication Nos. 2018/0125495, and 2017/0340351. Alternately, it is envisioned that the trans-anastomotic insertion device 100 could also be secured to a manually powered stapling device such as disclosed in U.S. Pat. No. 7,303,106 (the '106 Patent) or a stapling device that is configured for use with a robotic system such as disclosed in U.S. Pat. No. 9,962,159 that does not include a handle assembly.

FIG. 2 illustrates a distal portion of the stapling device 10 (FIG. 1) with the anvil assembly (not shown) removed and the insertion device 100 separated from the stapling device 10. The reload assembly 16 of the stapling device 10 includes a shell housing 20 and a staple cartridge 22 that is within the shell housing 20. The shell housing 20 includes an annular outer body portion 24 (FIG. 5) and an annular inner body portion 26 (FIG. 5) that define an annular cavity 28.

The inner annular body portion 26 defines a through bore 30 through which an anvil retainer (not shown) and an anvil shaft (not shown) of the anvil assembly (not shown) reciprocate as the anvil assembly (not shown) is moved between advanced and retracted positions to move the circular stapling device 10 between open and clamped positions. The inner annular body portion 26 has an inner wall 32 that includes shell splines 34 that engage splines on the anvil assembly (not shown) to properly orient the anvil assembly (not shown) with the staple cartridge 22 as the stapling device 10 is moved from the open position to the clamped position. The '106 Patent discloses components of a reload assembly 16 in further detail.

The staple cartridge 22 includes an annular body 40 that is received within the annular cavity 28 of the shell housing 20, the annular body 40 of the staple cartridge 22 defines a plurality of staple pockets 42 that receive staples (not shown). In aspects of the disclosure, the staple pockets 42 are arranged in two annular rows within the annular body 40 of the staple cartridge 22. It is envisioned that the annular body 40 of the staple cartridge 22 can have one or more annular rows of staple pockets 42.

Figure 3:
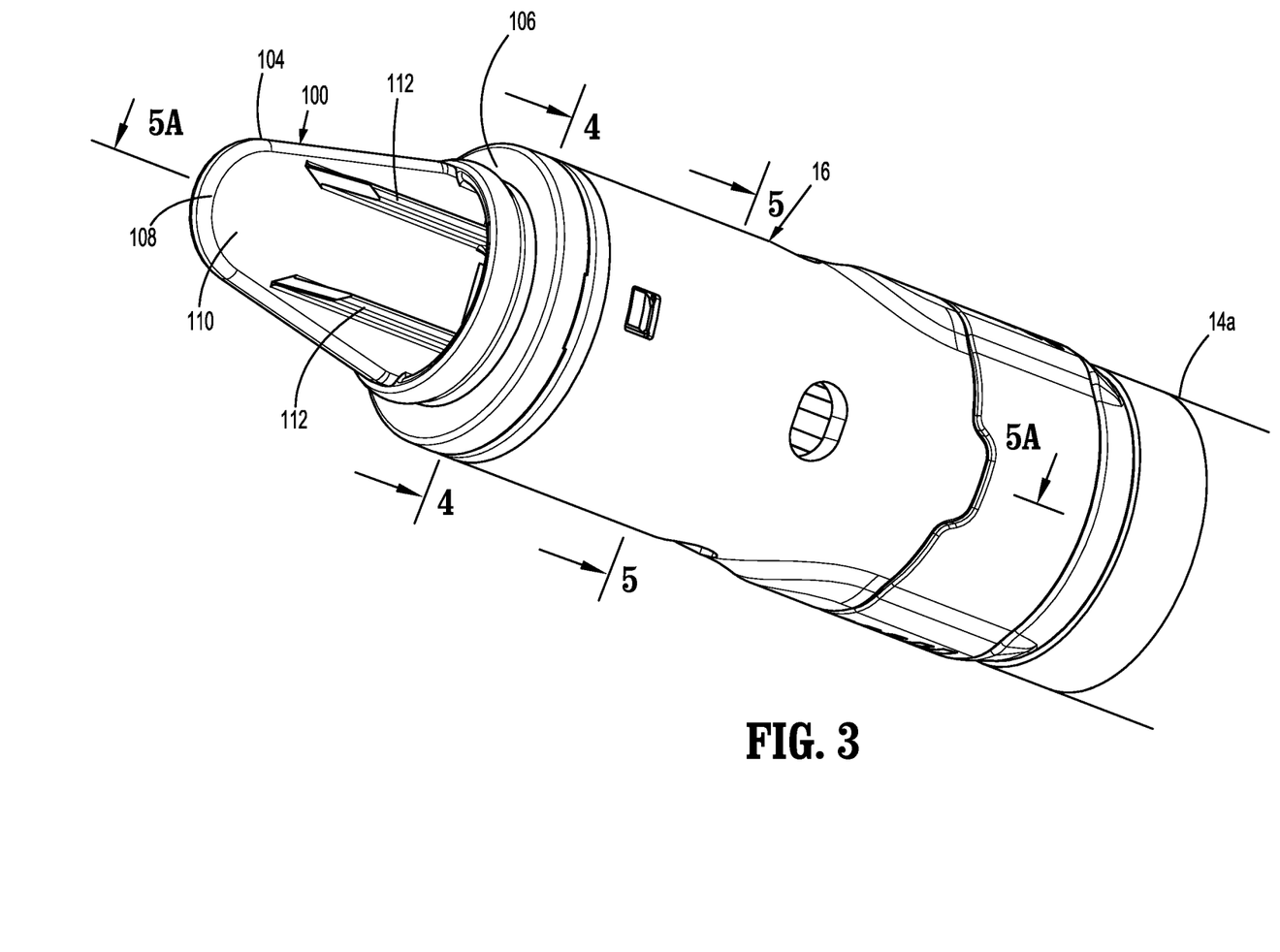
FIG. 3 is an enlarged view of the indicated area of detail shown in FIG. 1.

FIGS. 2 and 3 illustrate the insertion device 100 which includes a body 102 that defines a longitudinal axis "X" (FIG. 5A) and has a distal portion 104, a central portion 106, and a proximal portion 108. The distal portion 104 of the body 102 is triangularly shaped and includes a blunt or radiused distal end 109. In aspects of the disclosure, the distal portion 104 of the body 102 has planar side walls 110 that diverge outwardly in a direction towards the central portion 106 of the body 102 of the insertion device 100 such that the width of the side walls 110 is greatest adjacent the central portion 106. Each of the side walls 110 of the distal portion 104 includes longitudinal ribs 112 that extend along the side walls 110 to provide rigidity to the distal portion 104 of the insertion device 100.

The central portion 106 of the body 102 of the insertion device 100 has a shape that corresponds to the shape of the staple cartridge 22. In aspects of the disclosure, the central portion 106 of the insertion device 100 has a circular configuration and includes a proximal face 114 that is positioned and dimensioned to cover a distal face 22a of the staple cartridge 22 when the insertion device 100 is secured to the stapling device 10. It is envisioned that the staple cartridge 22 and the central portion 106 of the insertion device 100 may have configurations other than circular, e.g., oval. The proximal face 114 of the central portion 106 of the insertion device 100 includes a plurality of protrusions 116 that are received within the staple pockets 42 of the staple cartridge 22 when the insertion device 100 is secured to the stapling device 10 to secure the insertion device 100 in a rotatably fixed position in relation to the staple cartridge 22 on the reload assembly 16. In aspects of the disclosure, the central portion 106 of the insertion device 100 has a distal face 118 that supports an annular flange 118a that is positioned about the distal portion 104 of the insertion device 100. The annular flange 118a provides rigidity to the central portion 106 of the insertion device 110.

The proximal portion 108 of the insertion device 100 includes a central post 122 and an outer cylinder 124 that is positioned about the central post 122 (FIG. 2). In aspects of the disclosure, the central post 122 is hollow although it is envisioned that portions of the central post 122 could be solid. The central post 122 extends proximally from the central portion 106 of the insertion device 100 and includes a distal section 126 that extends from the central portion 106 of the insertion device 100 and a proximal section 128 that extends proximally from the distal section 126 of the proximal portion 108 of the insertion device 100. The proximal section 128 of the proximal portion 108 of the insertion device 100 includes splines 130 (FIG. 2) that are positioned about the central post 122 and are received between the shell splines 34 on the shell housing 20 when the insertion device 100 is attached to the reload assembly 16. Receipt of the splines 130 between the shell splines 34 aligns the protrusions 116 with the staple pockets 42 of the staple cartridge 22 when the insertion device 100 is secured to the reload assembly 16. In aspects of the disclosure, the central post 122 may support multiple splines 130, e.g., 3 to 8 splines. The proximal section 128 of the central post 122 of the insertion device 100 includes spaced legs 136 that extend proximally from the distal section 126 of the proximal portion 108 of the insertion device 100. Each of the legs 136 is resilient and includes a transverse extension 136a at its proximal end. The transverse extensions 136a define stop surfaces 140 that releasably engage a shelf 26a (FIG. 5A) defined within the shell housing 20 when the insertion device 100 is attached to the reload assembly 16 to releasably secure the proximal portion 108 of the insertion device 100 within the inner annular body portion 26 of the shell housing 20 as described in further detail below.

In aspects of the disclosure, the body 102 of the insertion device 100 is molded from a plastic material such as polyethylene or the like. The body 102 including the distal portion 104, the central portion 106, and the proximal portion 108 can be monolithically formed as a single piece. It is also envisioned that the portions of the insertion device 100 can be formed separately and secured together using known securement devices including adhesives, welding, fastening devices, interlocking elements to name a few.

Figure 4:
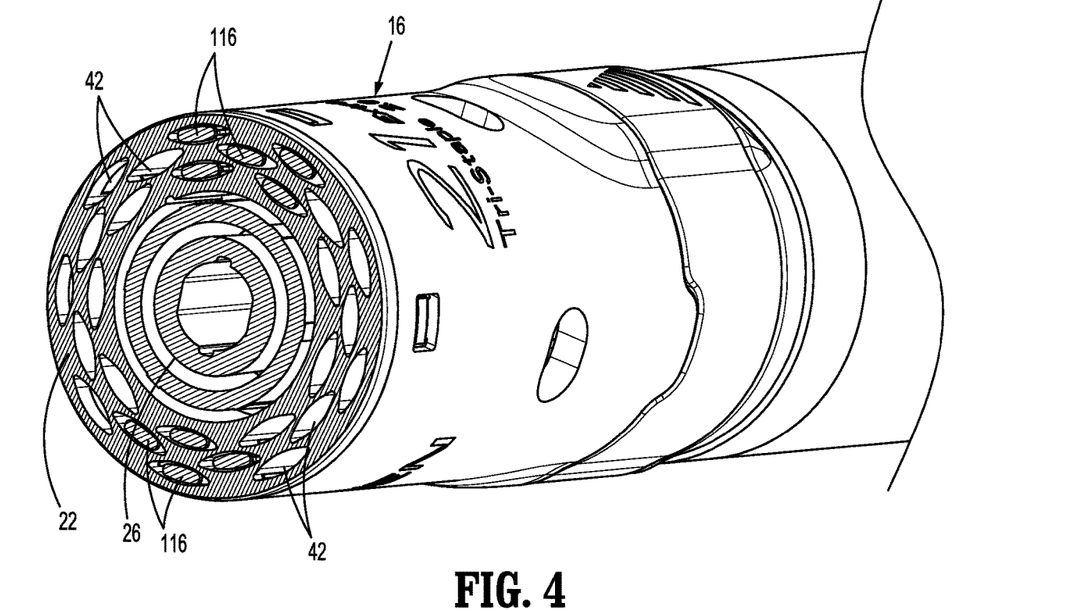
FIG. 4 is a cross-sectional view taken along section line 4-4 of FIG. 3.
Figure 5:
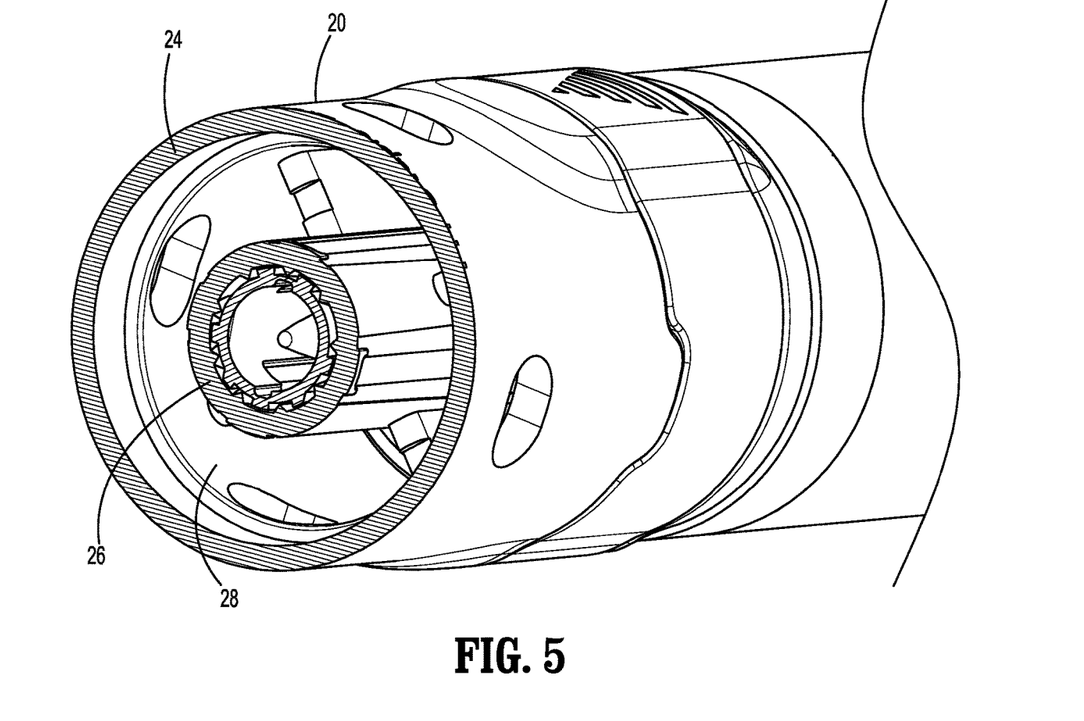
FIG. 5 is a cross-sectional view taken along section line 5-5 of FIG. 3.
Figure 5A:
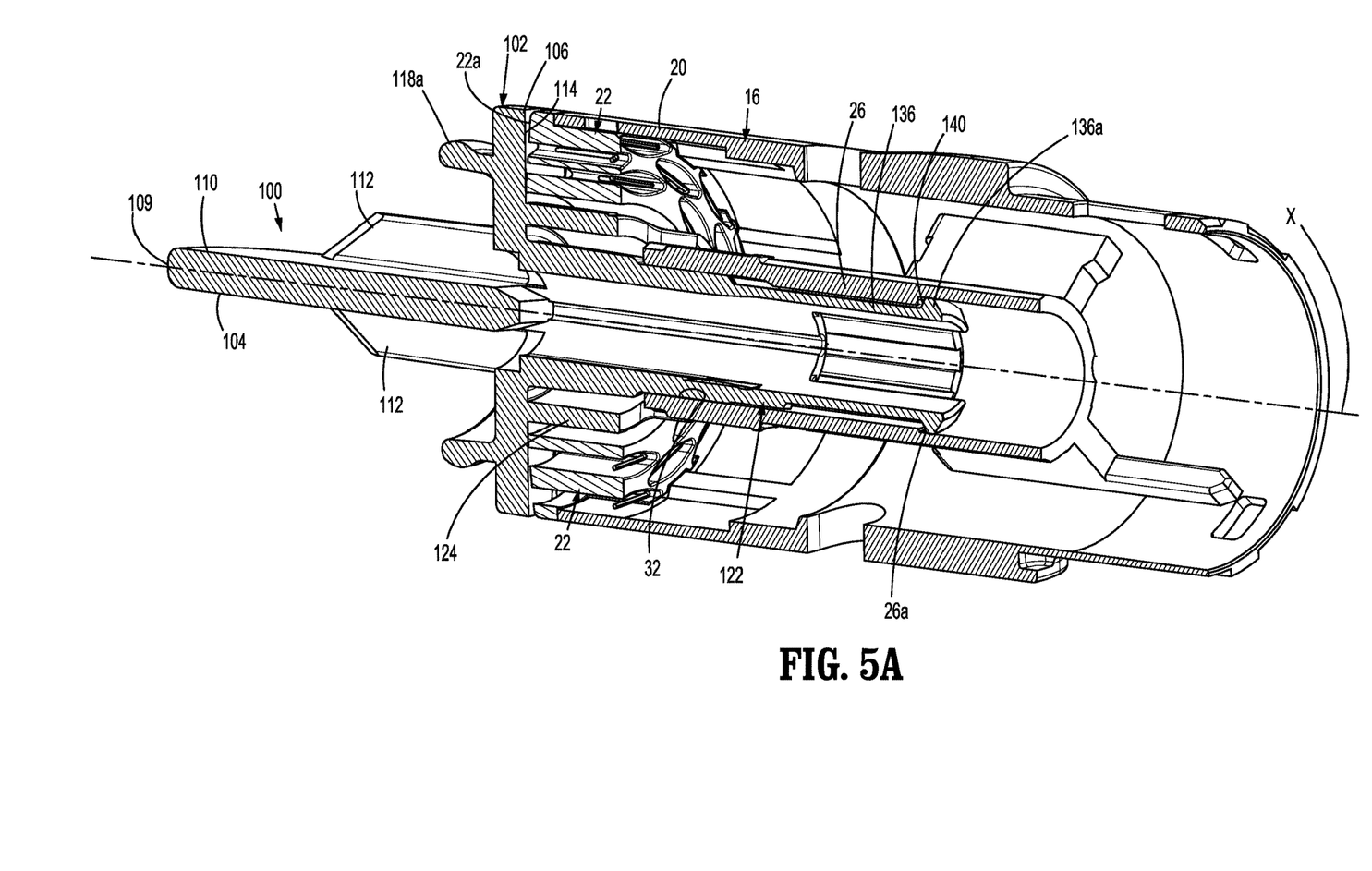
FIG. 5A is a cross-sectional view taken along section line 5A-5A of FIG. 3.

FIGS. 4-5A illustrate the insertion device 100 attached to the stapling device 10. When the insertion device 100 is attached to the reload assembly 16, the central post 122 of the proximal portion 108 of the insertion device 100 is inserted into the inner annular body portion 26 of the shell housing 20 in the direction of arrow "A" in FIG. 2. As the central post 122 is inserted into the inner annular body portion 26 of the shell housing 20, the splines 130 (FIG. 2) that are positioned about the central post 122 of the insertion device 100 are received between the shell splines 34 (FIG. 2) of the shell housing 20 to rotatably fix the insertion device 100 to the reload assembly 16. As the insertion device 100 is moved within the inner annular body portion 26 of the shell housing 20, the transverse extensions 136a on the proximal ends of the legs 136 of the insertion device 100 engage the inner wall 32 of the inner annular body portion 26 to deform the legs 136 of the central post 122 of the proximal portion 108 of the insertion device 100 inwardly. When the central post 122 is moved proximally within the inner annular body portion 26 of the shell housing 20 to a position in which the central portion 108 of the insertion device 100 engages the staple cartridge 22 of the reload assembly 16, the legs 136 flex outwardly to position the stop surfaces 140 on the transverse extensions 136a of the legs 136 move outwardly into engagement with the shelf 26a (FIG. 5A) of the inner annular body portion 26 to secure the central post 122 within the inner annular body portion 126 of the shell housing 20.

When the central portion 106 of the insertion device 100 engages the staple cartridge 22, the protrusions 116 on the proximal face 114 of the central portion 106 are received within the staple pockets 42 defined within the annular body 40 of the staple cartridge 22. As illustrated, when the insertion device 100 is attached to the stapling device 10, the outer cylinder 124 of the proximal portion 108 of the insertion device 100 is positioned about the inner annular body portion 26 of the shell housing 20. In this position, the protrusions 116 on the proximal face 114 of the central portion 106 of the insertion device 100 are received within the staple pockets 42 of the staple cartridge 22 and the central post 122 of the proximal portion 108 of the insertion device 100 is received within the inner annular body portion 26 of the shell housing 20.

Figure 6:
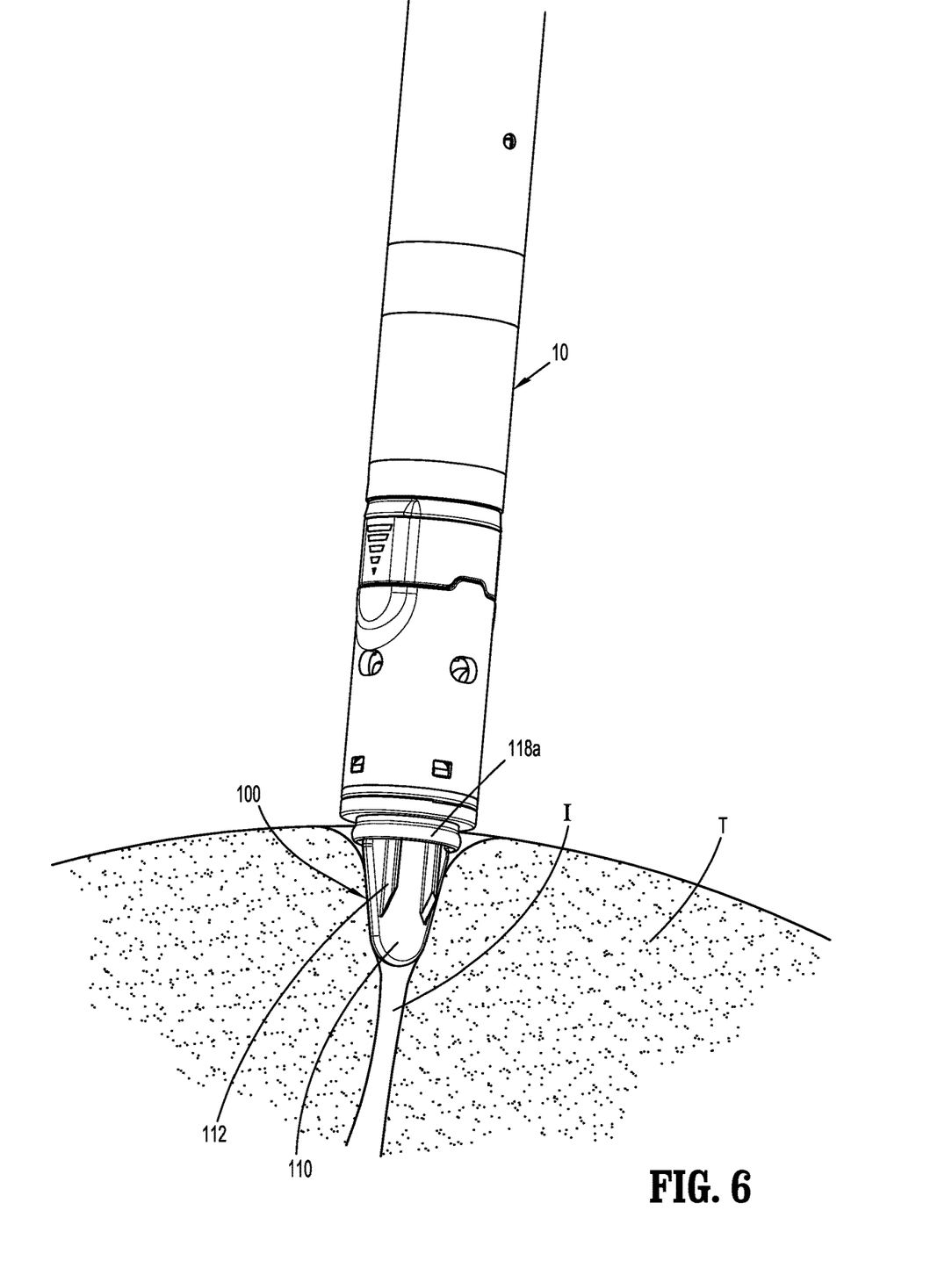
FIG. 6 is a side perspective view of the distal portion of the circular stapling device with the anvil assembly removed and the trans-anastomotic insertion device with the trans-anastomotic insertion device attached to the circular stapling device as the trans-anastomotic insertion device is inserted into an incision in a patient.

FIG. 6 illustrates the surgical stapling device 10 with the anvil assembly (not shown) removed and the insertion device 100 secured to the distal portion of the stapling device. As described above, when the insertion device 100 is supported on the stapling device 10, the proximal face 114 of the central portion 106 of the insertion device 100 is in juxtaposed opposition to the distal face 22a of the staple cartridge 22. When the insertion device 100 and the distal portion of the stapling device 10 are inserted through an incision "I" in tissue "T", the stapling device 10 and the insertion device 100 as an assembly may have to be twisted to distract the tissue "T" as the distal portion of the insertion device 100 is inserted through the incision "I". This may subject the insertion device 100 to high torsional forces. The receipt of the protrusions 116 on the central portion 106 of the insertion device 100, the splines 130 on the central post 122 of the proximal portion 108 of the insertion device 100, and the longitudinal ribs 112 on the distal portion 104 of the insertion device 100 provide added strength to the insertion device 100 to resist the high torsional forces that may be applied to the insertion device 100 during insertion of the surgical device 10 into a body cavity.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A trans-anastomotic insertion device comprising:
a body defining a longitudinal axis and including:
   a distal portion having a proximal end, a distal end, and a width that decreases from the proximal end towards the distal end, the distal end having a blunt distal surface, the distal portion including longitudinal ribs that extend between the proximal and distal ends of the distal portion;
   a central portion having a circular configuration and including a proximal surface and a distal surface, the proximal surface including a plurality of protrusions that extend proximally from the proximal surface; and
   a proximal portion having a central post that extends proximally from the central portion, the proximal portion including a plurality of longitudinally extending splines positioned about the central post.

2. The trans-anastomotic insertion device of claim 1, wherein the central portion includes an annular flange positioned on the distal surface about the distal portion.

3. The trans-anastomotic insertion device of claim 1, wherein the central post includes a proximal section having resilient legs.

4. The trans-anastomotic insertion device of claim 3, wherein each of the resilient legs includes a transverse extension that defines a stop surface.

5. The trans-anastomotic insertion device of claim 1, wherein the proximal surface of the central portion supports a cylinder that is positioned about and is spaced from the central post.

6. The trans-anastomotic insertion device of claim 5, wherein the body is molded from a plastic material.

7. The trans-anastomotic insertion device of claim 1, wherein the plurality of splines includes at least three splines.

8. The trans-anastomotic insertion device of claim 1, wherein the distal portion of the trans-anastomotic insertion device includes planar side walls, the longitudinal ribs positioned on the planar side walls.

9. A stapling device comprising:
a reload assembly including a shell housing and a staple cartridge, the shell housing having an annular inner body portion and an annular outer body portion, the annular inner body portion and the annular outer body portion defining an annular cavity, the staple cartridge supported on the shell housing within the annular cavity and including a body having a distal face and defining a plurality of staple pockets, the annular inner body portion having an inner wall including a plurality of splines; and
a trans-anastomotic insertion device including a body defining a longitudinal axis, the body including:
   a distal portion having a proximal end, a distal end, and a width that decreases from the proximal end towards the distal end, the distal end having a blunt distal surface, the distal portion including longitudinal ribs that extend between the proximal and distal ends of the distal portion;
   a central portion having a circular configuration and including a proximal surface and a distal surface, the proximal surface including a plurality of protrusions that extend proximally from the proximal surface; and
   a proximal portion having a central post that extends proximally from the central portion, the proximal portion including a plurality of longitudinally extending splines positioned about the central post;
the trans-anastomotic insertion device releasably secured to the reload assembly such that the central post is received within the annular inner body portion of the shell housing and the protrusions extending from the proximal face of the central portion of the trans-anastomotic insertion device are received within the staple pockets of the body of the staple cartridge.

10. The stapling device of claim 9, wherein the central portion of the body of the trans-anastomotic insertion device includes an annular flange positioned on the distal surface about the distal portion of the body of the trans-anastomotic insertion device.

11. The stapling device of claim 9, wherein the central post includes a proximal section having resilient legs.

12. The stapling device of claim 11, wherein each of the resilient legs includes a transverse extension that defines a stop surface and the annular inner body portion of the shell housing defines a shelf, the transverse extensions engaging the shelf to retain the trans-anastomotic insertion device on the reload assembly.

13. The stapling device of claim 9, wherein the proximal surface of the central portion supports a cylinder that is positioned about and is spaced from the central post.

14. The stapling device of claim 13, the cylinder is positioned about and engaged with the annular inner body portion of the shell housing when the trans-anastomotic insertion device is secured to the reload assembly.

15. The stapling device of claim 9, wherein the body is molded from a plastic material.

16. The stapling device of claim 9, wherein the plurality of splines includes at least three splines.

17. The stapling device of claim 9, further including an elongate body having a proximal portion and a distal portion, the reload assembly supported on the distal portion of the elongate body.

18. The stapling device of claim 9, further including a handle assembly, the proximal portion of the elongate body coupled to the handle assembly.

19. The stapling device of claim 18, wherein the handle assembly includes a stationary handle and actuation buttons.

20. The stapling device of claim 9, wherein the distal portion of the trans-anastomotic insertion device includes planar side walls, the longitudinal ribs positioned on the planar side walls.

\* \* \* \* \*